(12) United States Patent
Morris et al.

(10) Patent No.: US 7,429,462 B2
(45) Date of Patent: Sep. 30, 2008

(54) KITS FOR ASSAYS OF RAPID SCREENING OF DIABETES

(75) Inventors: Carol Ann Morris, Duluth, GA (US); Fiona Patricia Carney, Atlanta, GA (US); Jennifer Dawn Lane, Stone Mountain, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/706,809

(22) Filed: Feb. 15, 2007

(65) Prior Publication Data

US 2007/0154395 A1 Jul. 5, 2007

Related U.S. Application Data

(62) Division of application No. 10/706,208, filed on Nov. 12, 2003, now abandoned.

(60) Provisional application No. 60/427,705, filed on Nov. 20, 2002.

(51) Int. Cl.
*C12Q 1/54* (2006.01)

(52) U.S. Cl. ....................................................... 435/14

(58) Field of Classification Search ........................ None
See application file for complete search history.

(56) References Cited

U.S. PATENT DOCUMENTS

| 5,122,362 A | 6/1992 | Phillips et al. | 424/9 |
| 2001/0034500 A1* | 10/2001 | March | 604/66 |

FOREIGN PATENT DOCUMENTS

| SU | 1534406 A1 | 11/1987 |
| WO | WO 99/35520 A1 * | 7/1999 |
| WO | WO 02/03855 A1 | 1/2002 |
| WO | WO 02/087429 A1 * | 11/2002 |

OTHER PUBLICATIONS

European Search Report.
A Fluorescence-Based Glucose Biosensor Using Concanavalin A and Dextran Encapsulated in a Poly (ethylene gylcol) Hydrogel, Ryan J. Russell and Michael V. Pishko, Analytical Chemistry, vol. 71, No. 15, Aug. 1, 1999.

* cited by examiner

*Primary Examiner*—Ralph Gitomer
*Assistant Examiner*—Amanda P Wood
(74) *Attorney, Agent, or Firm*—Sheng-Hsin Hu; Jian Zhou

(57) ABSTRACT

The invention provides an in vivo screening assay and an in vitro screening assay for rapid screening of diabetes. A method of the invention includes determining a first glucose concentration in an ocular fluid of a patient; administering orally a load of carbohydrate to the patient; determining a second glucose concentration in an ocular fluid of the patient at a period of time of less than 50 minutes after orally administering of the load of carbohydrate; comparing the second glucose concentration with the first glucose concentration to determine if the patient is likely to be a diabetic. The method of the invention is performed by using a kit of the invention. The kit comprises: (1) a glucose-sensing ophthalmic device and instructions for using the glucose-sensing ophthalmic device to screen for diabetes; or (2) two or more tear-collecting devices, and a testing agent composition which specifically reacts with glucose to form a detectable signal. The glucose-sensing ophthalmic device comprises a testing agent composition which specifically and reversibly interacts with glucose to form a detectable optical signal which changes in a concentration-dependent manner.

3 Claims, 1 Drawing Sheet

KITS FOR ASSAYS OF RAPID SCREENING OF DIABETES

This application is a division of U.S. patent application Ser. No. 10/706,208 filed Nov. 12, 2003 now abandoned, which claims under 35 USC § 119 (e) the benefit of the filing date of U.S. Provisional Patent Application Ser. No. 60/427,705 filed Nov. 20, 2002 and all references incorporated therein.

The invention is related to methods and kits for rapid screening of diabetes.

BACKGROUND OF THE INVENTION

Diabetes is a serious, lifelong disease which can cause long-term complications that affect almost every part of the body. This disease often leads to blindness, heart and blood vessel disease, strokes, kidney failure, amputations, and nerve damage. Uncontrolled diabetes can complicate pregnancy, and birth defects are more common in babies born to women with diabetes. Diabetes is widely recognized as one of the leading causes of death and disability in the United States.

It is believed that earlier diagnosis and treatment can prevent or delay the costly and burdensome complications of diabetes. Currently, about 5 to 6 million adults in the United States have diabetes but do not know it. The simpler testing method of measuring fasting glucose should help identify these people so they can benefit from treatment sooner. Traditionally, the criteria for diagnosing diabetes relied heavily on performing an oral glucose tolerance test (OGTT). In this test, the person must come in fasting, drink a glucose syrup, and have a blood sample taken 2 hours later. This complicated procedure made detection and diagnosis of diabetes a difficult and cumbersome process. Recently, it is recommended that OGTT be eliminated from clinical use and that fasting plasma glucose is used for detection and diagnosis of diabetes. A fasting blood glucose of 126 mg/dL or greater is the value to diagnose diabetes since this value has been found to be associated with an increased risk of diabetes complications affecting the eyes, nerves, and kidneys. For such test, a patient still needs to come in fasting and is forced to draw blood and to endure discomfort associated with needles to obtain blood samples for testing fasting blood glucose level. Blood samples are generally to be sent to a specialized laboratory for testing and it typically take a couple of days to obtain the testing results. If the testing results show a fasting blood glucose of 126 mg/dL or greater, that patient needs to undergo a second test to confirm the diagnosis. Although the fasting value can be easily obtained during routine physician visits, in clinics at the place of employment, and other situations, a fasting test may still be inconvenient, uncomfortable, and cumbersome. Therefore, there is still a need for a diabetes-screening method which is fast and can alleviate the discomfort and inconvenience for patients.

SUMMARY OF THE INVENTION

One object of the invention is to provide a method for rapid screening of diabetes.

Another object of the invention is to provide kits for rapid screening of diabetes.

These and other objects of the invention are met by the various aspects of the invention described herein.

The invention, in one aspect, provides a method for rapidly screening for diabetes, the method comprising the steps of: collecting a first tear fluid from a patient using a first tear-collecting device; assaying a specific amount of the first tear fluid to determine a first glucose concentration; administering orally a load of carbohydrate to the patient; collecting a second tear fluid, at a period of time of less than 50 minutes after orally administering of the load of carbohydrate, using a second tear-collecting device; assaying a specific amount of the second tear fluid to determine a second glucose concentration; comparing the second glucose concentration with the first glucose concentration to determine if the patient is likely to be a diabetic.

The invention, in another aspect, provides a method for rapidly screening diabetes, the method comprising the steps of: contacting a glucose-sensing ophthalmic device with an ocular fluid, wherein the glucose-sensing ophthalmic device comprises a testing agent composition which specifically and reversibly interacts with glucose to form a detectable signal which changes in a concentration-dependent manner; determining by means of the glucose-sensing ophthalmic device a first glucose concentration in the ocular fluid; administering orally a load of carbohydrate to the patient; at a period of time of less than 50 minutes after orally administering of the load of carbohydrate, determining by means of the glucose-sensing ophthalmic device a second glucose concentration in the ocular fluid; and comparing the second glucose concentration with the first glucose concentration to determine if the patient is likely to be a diabetic.

The invention, in a still further aspect, provides a kit for screening for diabetes, the kit comprising: (1) a glucose-sensing ophthalmic device, wherein the glucose-sensing ophthalmic device comprises a testing agent composition which specifically and reversibly interacts with glucose to form a detectable signal which changes in a concentration-dependent manner; or (2) two or more tear-collecting devices selected from the group consisting of a strip, a capillary tube, and a soft-hydrogel contact lens, and a testing agent composition which specifically reacts or interacts with glucose to form a detectable signal which changes in a concentration-dependent manner, wherein said strip has a first end and an opposite second end and preferably has substantially uniform cross-sections from the first end to the second end, wherein said strip is made of a hydrogel material in a substantially dry state and is characterized by having a substantially uniform swelling along the hydrogel strip from the first end to the second end when fully wicked by a tear fluid and by having a correlation between the volume of tear uptake by said strip and the length of a tear-wicked end portion of said strip.

DETAILED DESCRIPTION OF PREFERRED EMBODIMENTS

Figure 1:
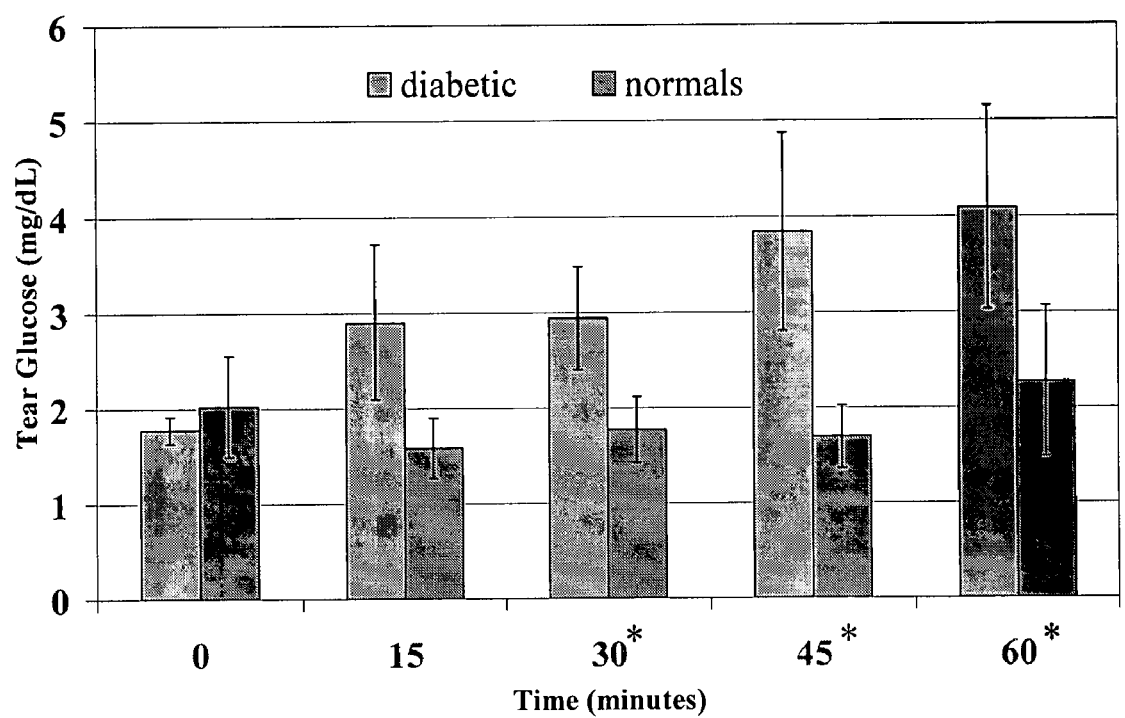
FIG. 1 shows glucose concentrations in a tear fluid collected at every 15 minutes after oral administration of a carbohydrate load to a subject.

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

The invention, in one aspect, provides a method for rapidly screening for diabetes, the method comprising the steps of: collecting a first tear fluid from a patient using a first tear-collecting device; assaying a specific amount of the first tear fluid to determine a first glucose concentration; administering orally a load of carbohydrate to the patient; collecting a second tear fluid, at a period of time of less than 50 minutes after orally administering of the load of carbohydrate, using a second tear-collecting device; assaying a specific amount of the second tear fluid to determine a second glucose concentration; comparing the second glucose concentration with the first glucose concentration to determine if the patient is likely to be a diabetic.

Any tear-collecting device known to a person skilled in the art can be used. Examples of tear-collecting devices are glass capillary tubes, hydrogel strips, and contact lenses.

Preferably, a tear-collecting device is a hydrogel strip, which is disclosed in a copending U.S. patent application Ser. No., entitled "Methods and Kits For Assays Of Analytes Of Interest In Tears", filed on Oct. 1, 2002, herein incorporated by reference in its entirety. The hydrogel strip is made of a hydrogel material in substantially dry state and has a uniform cross-section, wherein said strip is characterized by having a substantially uniform swelling along the hydrogel strip when fully wicked by a tear fluid and characterized by having a defined correlation between the volume of tear uptake by said strip and the length of the tear-wicked end portion of said strip. A hydrogel strip as a tear-collecting device can offer some advantages over a glass capillary tube, including, for example, easy of handling, safety, and low irritation. Furthermore, assays for glucose in an ocular fluid can be carried out directly on and in one or more divided pieces of the tear-wicked portion of a hydrogel strip. Or, a tear fluid absorbed by a hydrogel strip can be substantially recovered by a method known to a person skilled in the art.

A "hydrogel material" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "monomer" means a low molecular weight compound that can be polymerized. Low molecular weight typically means average molecular weights less than 700 Daltons.

A "macromer" refers to a medium and high molecular weight compound or polymer that contains functional groups capable of further polymerization. Medium and high molecular weight typically means average molecular weights greater than 700 Daltons.

A "hydrophilic vinylic monomer" refers to a monomer which as a homopolymer typically yields a polymer that is water-soluble or can absorb at least 10 percent by weight water. Suitable hydrophilic vinylic comonomers include, without limitation, hydroxy-substituted lower alkylacrylates and -methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkylvinyl-ethers, sodium ethylene sulphonate, sodium styrene sulphonate, 2-acrylamido-2-methyl-propane-sulphonic acid, N-vinyl pyrrole, N-vinyl succinimide, N-vinyl pyrrolidone, 2- or 4-vinyl pyridine, acrylic acid, methacrylic acid, amino- (whereby the term "amino" also includes quaternary ammonium), mono-lower-alkylamino- or di-lower-alkylamino-lower-alkyl-acrylates and -methacrylates, allyl alcohol and the like. Preference is given e.g. to hydroxy-substituted $C_2$-$C_4$-alkyl(meth)acrylates, five- to seven-membered N-vinyl-lactams, N,N-di-$C_1$-$C_4$-alkyl-methacrylamides and vinylically unsaturated carboxylic acids with a total of 3 to 5 carbon atoms. Examples of suitable hydrophilic vinylic comonomers include hydroxyethyl methacrylate, hydroxyethyl acrylate, acrylamide, methacrylamide, dimethylacrylamide, allyl alcohol, vinyl pyridine, vinyl pyrrolidone, glycerol methacrylate, N-(1,1-dimethyl-3-oxobutyl) acrylamide, and the like.

Any known, suitable hydrogels can be used in the invention. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, silicone-containing hydrogels, polyurethane, polyurea, and the like. A hydrogel can be prepared according to any methods known to a person skilled in the art.

Preferably, a hydrogel strip is placed at a location near the lateral canthus of an eye to collect tear fluids. "Lateral canthus" refers to one of the two canthuses of an eye, which is located away from the nose.

A hydrogel strip can have any dimension suitable for collecting tear fluids. A hydrogel strip of the invention has a length sufficient long to absorb a minimum volume of tear (e.g., at least about 1 µl). A hydrogel strip is preferably at least 15 mm in length, more preferably at least 30 mm in length.

Preferably, the dimension of the cross-section (e.g, diameter, width, height, etc.) of a hydrogel strip is neither too small nor too large. Where the dimension of the cross-section of a hydrogel strip is too small, the hydrogel strip becomes not structurally steady and/or can become sharp so that it can potentially cause damages to eye tissues. Where the dimension of the cross-section of a hydrogel strip is too large, the hydrogel strip can not access the lateral canthus.

A hydrogel strip preferably has a uniform cross-section along the strip. The cross-section of a hydrogel strip of the invention can have any geometric shape, for example, such as rectangular, square, circular, triangular, annular ring, or the like. Preferably, the cross-section of a hydrogel strip has a rectangular shape. The rectangular cross-section has a width of from about 1 mm to about 3 mm, preferably from 1.5 mm to 2 mm, and a height of from 0.5 mm to 1.5 mm, preferably from 0.8 mm to 1.2 mm. Where the cross-section of a hydrogel strip of the invention is circular, the diameter of the circular cross-section is preferably from 1 mm to 3 mm, more preferably from 1.5 mm to 2.2 mm.

A "substantially uniform swelling along the hydrogel strip when fully wicked by a tear fluid" means that when a hydrogel strip is fully wicked by a fluid (e.g., a tear), it has a substantially uniform increase in volume along the length of the hydrogel strip and no significant change in the geometric shape of the strip can be observed.

Correlation between the volume of fluid (e.g., tear) uptake by said strip and the length of the fluid-wicked end portion of said strip preferably is a substantially linear relationship. With a substantially linear correlation, the volume of tear uptake by a hydrogel strip can be easily quantified. In a preferred embodiment, the volume of tear uptake is noticeably marked on a hydrogel strip.

For example, a hydrogel strip is prepared from poly(vinyl alcohol) (PVA) and has a dimension of 1.5 mm in width, 1.0 mm in height, and 30 mm in length.

Glucose can be assayed directly on a fraction or all of the tear-wicked portion of the strip or by first recovering the tear sample from the wicked portion of the strip and then assaying glucose in the recovered tear sample.

It is well known to a skilled artisan that the assay of glucose can be carried out with the help of a testing agent composition which specifically reacts or interacts with glucose, leading to formation of a detectable signal. A detectable signal, for example, can be electrical signals (electrochemical assays), or optical signals (enzyme assays, binding assays or competitive binding assays). Exemplary electrical signals are electrical potentials and currents. "Optical signals" refer to changes in the optical properties, including, but not limited to, a color formation, a change in color, fluorescence, luminescence, chemiluminescence, changes in fluorescence or luminescence intensity, changes in fluorescence or luminescence lifetimes, fluorescent anisotropy or polarization, a spectral shift of the emission spectrum, time-resolved anisotropy decay, and the like.

Electrochemical assay of glucose is largely carried out by using an enzymatic electrode (or biosensor) which consists of a thin layer of enzymes adsorbed to the active surface of a transducer. Along with a suitable reference electrode and a circuit, a biosensor allows to measure either the potential difference generated between the two electrodes (for potentiometric measurements) or the current that flows between the two electrodes (for amperometric measurements). For, example, a glucose biosensor consists of a carbon electrode with a conductive coating containing a mixture of glucose oxidase and mediator (e.g., ferrocene or derivatives thereof (see, for example, Cass et al., "Ferrocene-mediated Enzyme Electrode for Amperometric Determination of Glucose", Anal. Chem. 56: 667-671 (1984), herein incorporated any reference in its entirety). At the working electrode surface glucose is oxidized by the glucose oxidase enzyme. This reaction causes the mediator to be reduced. At the fixed potential, applied between the two electrodes the mediators is oxidized, generating a signal response which correlates with the glucose concentration in a sample.

The hydrogel strip can be served as a medium for performing an electrochemical assay. For example, the electrochemical assay of glucose in a tear fluid can be carried out by first collecting an amount of the tear fluid using a hydrogel strip, then by placing the whole or fractional tear-wicked portion of the hydrogel strip in direct contact with an enzyme electrode and a reference electrode, and finally by applying a fixed potential between the two electrodes to obtain an amperometric signal (current) that correlates with the concentration of the analyte of interest.

Glucose can be assayed based on the Trinder reaction. Typically in the Trinder reaction, glucose oxidase, in the presence of oxygen, oxidizes glucose to form gluconic acid and hydrogen peroxide which in turn reacts with a chromogenic oxidation/reduction indicator (e.g., phenol, 3-hydroxy-2, 4,6-triiodobenzoic acid, 3-hydroxy-2,4,6-tribromobenzoic acid, etc.) in the presence of peroxidase to form a color different from its original color or to generate a chemiluminescence.

Binding assays and competitive binding assays have been widely used in the determination of an analyte of interest in a sample. Typically, a binding assay (without use of any competitor) is generally carried out by using a protein or fragment thereof or a chemical compound (as a receptor) that is capable of binding said analyte (ligand) in said sample and has a detectable optical signal (or other detectable signal) that changes in a concentration-dependent manner when the receptor is bound to said analyte. A competitive binding assay is based on the competition between a labeled ligand (analyte) or ligand analogue (analyte-analogue) and an unlabeled ligand (analyte) in the reaction with a receptor (e.g., antibody, receptor, transport protein, chemical compound). The labeled ligand (analyte) or ligand analogue (analyte-analogue) also is called as a competitor.

The detectable optical signal results from one or more labels associated with a receptor and/or a competitor. A label may be covalently or non-covalently bound to a receptor or a competitor. A "receptor" refers to a protein or fragment thereof or a chemical compound that is capable of binding reversibly glucose in a sample. A "competitor" refers to a molecule or moiety that competes with glucose for binding to a receptor.

A wide range of suitable labels are known. For example, the label may be a fluorescent label. "A fluorescent label" refers to a moiety that comprises at least one fluorophore and that, when attached to a molecule, renders such molecules detectable using fluorescent detection means. Exemplary fluorophores include xanthene-type dyes, fluorescein-type dyes, rhodamine-type dyes, cyanine-type dyes, and the like. A fluorophore can also be a fluorescent protein such as phycobiliproteins.

The detectable optical signal can be derived from a pair of fluorophores, a first fluorophore and a second fluorophore. One of the two fluorophores can be an energy donor, for example the first fluorophore, which absorbs energy upon excitation at an excitation wavelength within its absorption spectrum and emits energy at a wavelength within its emission spectrum, and the other fluorophore can be an energy acceptor, for example the second fluorophore, which accepts the energy emitted by the donor at a wavelength within the absorption spectrum of the acceptor and emits energy at a wavelength within the emission spectrum of the acceptor. The wavelength of the absorption maximum of the donor fluorophore is shorter than the wavelength of the absorption maximum of the acceptor fluorophore; and the wavelength of the emission maximum of the donor fluorophore is shorter than the wavelength of the emission maximum of the acceptor fluorophore. It is known that the energy transfer efficiency depends on the several factors such as spectral overlap between the emission spectrum of the donor and the absorption spectrum of the acceptor, spatial distance between donor and acceptor fluorophores, relative orientation of donor and acceptor fluorophore, quantum yield of the donor and excited state lifetime of the donor. It is well known to a person skilled in the art how to select a donor fluorophore and a acceptor fluorophore. In a binding assay system, the energy donor fluorophore and the energy acceptor fluorophore each can be bound to a receptor and spaced such that there is a detectable optical signal when the receptor is bound to the analyte. In a competitive binding assay system, one of the energy donor fluorophore and the energy acceptor fluorophore can be bound to the receptor and the other can be bound to the competitor.

It is understood that the above energy acceptor fluorophore can be replaced by a non-fluorescent energy transfer acceptor, for example, such as a dye which accepts the energy emitted by the donor fluorophore at a wavelength within the absorption spectrum of the acceptor but does not emits energy in the form of fluorescence or luminescence.

A fluorescent label can intrinsically be part of the receptor. For example, a receptor can be a fusion protein comprising at least the fluorescent part of a fluorescent protein and at least the binding part of a receptor protein. Alternatively, the fluorescent label can be a fluorescent label which is not naturally associated with the receptor moiety but which is attached by means of a chemical linkage, such as a covalent bond.

A fluorescent label can intrinsically be part of the competitor. Alternatively, the fluorescent label can be a fluorescent label which is not naturally associated with the competitor moiety but which is attached by means of a chemical linkage, such as a covalent bond.

One example of binding assay is an assay for glucose disclosed in U.S. Pat. No. 6,197,534, using an *E. coli* glucose/galactose binding protein ("GGBP") as previously described (Scholle, et al., *Mol. Gen. Genet.* 208:247-253 (1987)), or functionally equivalent fragments thereof. As a sensor for glucose monitoring, GGBP has several favorable features including a single glucose binding site and high affinity for glucose; GGBP binds glucose with a dissociation constant near 0.8 µM. Like similar transport proteins from other bacteria, GGBP is highly specific for binding glucose and/or galactose. The apparent binding affinity of GGBP for sugars other than glucose or galactose is typically 100-1000 fold weaker [Boos, et al., *J. Biol. Chem.* 247(3):917-924 (1972); Boos, W., *J. Biol. Chem.* 247(17):5414-5424 (1972); Strange and Koshland, *Proc. Nat'l Acad. Sci. USA* 73(3):762-766 (1976); Zukin, et al., *Biochemistry* 16(3):381-386 (1977)). The high affinity for glucose also will allow to measure µM glucose concentrations in a tear fluid. GGBP can be labeled with one fluorescence energy donor moiety and one fluorescence energy acceptor at two specific position on GGBP in a manner so that there is a detectable spectral change (e.g., change in fluorescence intensity or lifetime) when GGBP is bound to glucose.

One example of a competitive binding assay is a glucose assay disclosed in U.S. patent application Ser. No. 09/784,471 (herein incorporated by reference), using a glucose-sensing system which comprises tetramethylrhodamine isothiocyanate concanavalin A (TRITC-ConA) as a receptor, fluorescein isothiocyanate dextran (FITC-dextran) as a competitor. While the FITC-dextran is bound to the TRITC-ConA, the FITC fluorescence is quenched by TRITC via a fluorescence resonance energy transfer. Increased glucose concentration frees the FITC-dextran and results in fluorescence which is proportional to glucose concentration.

The hydrogel strip can be served as a medium for performing a binding assay or a competitive binding assay using a testing agent composition which specifically reacts or interacts with glucose to form a detectable signal that changes in a concentration-dependent manner.

Where glucose in a tear fluid is assayed based on a binding assay, the testing agent composition preferably comprises a receptor that is capable of binding glucose and has a detectable optical signal that changes in a concentration-dependent manner when the receptor is bound reversibly to glucose, wherein said detectable optical signal results from one or more labels associated with the receptor. More preferably, the testing agent composition comprises: (1) a fluorescence energy donor and a fluorescence energy acceptor; or (2) a fluorescence energy donor and a non-fluorescence energy acceptor.

Where glucose in a tear fluid is assayed based on a competitive binding assay, the testing agent composition preferably comprises a receptor having a first label associated therewith, a competitor having a second label associated therewith, wherein one of the first and second labels is a fluorescent energy donor and the other one is a fluorescent or non-fluorescent energy acceptor. Binding of both the competitor and glucose to the receptor is reversible.

A testing agent composition can be a solution or can be incorporated partially or fully in a hydrogel strip. For example, the receptor can be covalently bound to the strip material. The receptor can be covalently linked to the strip material according to any known, suitable methods.

Similarly, a competitor can be tethered, preferably via a flexible linker, to the strip material according to any known, suitable methods. Introduction of flexible linkers into a polymer or a competitor or receptor is known to a person skilled in the art.

Any known suitable competitor can be used in the competitive binding assays of glucose. For example, a glucose competitor can be a dextran (which competes with glucose for binding to Concanavalin A). Another exemplary glucose competitors are 2-deoxy-D-glucose, D-mannose and D-galactose (which competes with glucose for binding to inactivated glucose oxidase). Further exemplary glucose competitors are glucose-protein conjugates (such as a conjugate of glucose and albumin, obtained by covalently attaching glucose onto the surface of albumin).

Exemplary receptors for glucose include, but are not limited to Concanavalin A (Mansouri & Schultz, *Bio/Tech* 2, 385, 1984), GGBP, inactivated glucose oxidase (e.g., apo-glucose oxidase or the like), inactivated glucose dehydrogenase (e.g., apo-glucose dehydrogenase or the like), boronic acid, or a genetically engineered glucose binding protein or fragments thereof.

Preferably, at least one component or all components of a testing agent composition can be impregnated in a hydrogel strip for rapidly screening for diabetes.

Detectable signals can be detected by any method known to a person skilled in the art. For example, if the label is a luminescent label, the detector may include a luminometer; if the label is a colorimetric label, the detector may include a calorimeter; if the label is a fluorescent label, the detector may include a fluorophotometer. Construction of such devices is well known in the art. Light with wavelengths which will excite the fluorescent label can be provided, for example, by a laser or a light source, such as a light-emitting diode.

The invention, in another aspect, provides a method for rapidly screening of diabetes, the method comprising the steps of: contacting a glucose-sensing ophthalmic device with an ocular fluid, wherein the glucose-sensing ophthalmic device comprises a testing agent composition which specifically and reversibly interacts with glucose to form a detectable signal which changes in a concentration-dependent manner; determining by means of the glucose-sensing ophthalmic device a first glucose concentration in the ocular fluid; administering orally a load of carbohydrate to the patient; at a specific period of time (less than 50 minutes) after orally administering the load of carbohydrate, determining by means of the glucose-sensing ophthalmic device a second glucose concentration in the ocular fluid; and comparing the second glucose concentration with the first glucose concentration to determine if the patient is likely to be a diabetic.

In a preferred embodiment, the glucose-sensing ophthalmic device comprises a receptor (e.g., a protein or fragment thereof or a chemical compound) that is capable of binding glucose and has a detectable optical signal that changes in a concentration-dependent manner when the receptor is bound to glucose, wherein said detectable optical signal results from one or more labels associated with the receptor. More preferably, the detectable optical signal results from: (1) a fluorescence energy donor and a fluorescence energy acceptor; or (2) a fluorescence energy donor and a non-fluorescence energy acceptor, wherein the energy donor and acceptor are associated with the receptor. As described above, a fluorescent energy donor can be a fluorescent label; a fluorescent energy acceptor can be a fluorescent label; and a non-fluorescent energy donor can be a dye moiety.

An "ophthalmic device", as used herein, refers to a contact lens (hard or soft), an intraocular lens, a corneal onlay, other ophthalmic devices (e.g., stents, implants, or the like) used on or about the eye or ocular vicinity, and cases or containers for storing ophthalmic devices or ophthalmic solutions.

A fluorescent energy acceptor and/or acceptor can intrinsically be part of the receptor. For example, a receptor can be a fusion protein comprising at least the fluorescent part of a fluorescent protein and at least the binding part of a receptor protein. Alternatively, the fluorescent label can be a fluorescent label which is not naturally associated with the receptor moiety but which is attached by means of a chemical linkage, such as a covalent bond.

In another preferred embodiment, the glucose-sensing ophthalmic device comprises a receptor having a first label associated therewith, a competitor having a second label associated therewith, wherein one of the first and second labels is a fluorescent energy donor and the other one is a fluorescent or non-fluorescent energy acceptor. Binding of both the competitor and glucose to the receptor is reversible. Exemplary glucose-sensing ophthalmic devices are those disclosed in copending U.S. patent application Ser. No. 09/784,471 (herein incorporated by reference).

A fluorescent energy donor can intrinsically be part of the receptor. For example, a receptor can be a fusion protein comprising at least the fluorescent part of a fluorescent protein and at least the binding part of a receptor protein. Alternatively, the fluorescent energy donor can be a fluorescent label which is not naturally associated with the receptor moiety but which is attached by means of a chemical linkage, such as a covalent bond.

A fluorescent or non-fluorescent energy acceptor can intrinsically be part of the competitor. Alternatively, the fluorescent or non-fluorescent energy acceptor can be a fluorescent label or dye which is not naturally associated with the competitor moiety but which is attached by means of a chemical linkage, such as a covalent bond.

A variety of options are available for providing the receptor and competitor moieties in an ophthalmic lens. Construction of various types of ophthalmic devices is well known in the art. Construction of contact lenses is taught, for example, in U.S. Pat. Nos. 5,965,631, 5,894,002, 5,849,811, 5,807,944, 5,776,381, 5,426,158, 4,099,859, 4,229,273, 4,168,112, 4,217,038, 4,409,258, 4,388,164, 4,332,922, 4,143,949, 4,311,573, 4,589,964, and 3,925,178.

Construction of intraocular lens implants is taught, inter alia, in U.S. Pat. Nos. 6,051,025, 5,868,697, 5,762,836, 5,609,640, 5,071,432, 5,041,133, and 5,007,928. Subconjunctival lenses are taught, for example, in U.S. Pat. Nos. 5,476,511, 5,400,114, and 5,127,901. Intracorneal lenses are taught, inter alia, in U.S. Pat. Nos. 6,090,141, 5,984,961, 5,123,921, and 4,799,931.

The receptor and/or receptor can be covalently bound or tethered to the ophthalmic device material which comprises a polymer meshwork containing pores. The pores are of a size which permit glucose to be bound reversibly to the receptor.

The receptor can be covalently linked to a polymer meshwork according to any known, suitable methods. A polymer meshwork can comprise or be modified to comprise reactive moieties such as groups containing amine, hydroxy, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)proprionamide, glyoxal and aldehyde. For example, a cyclic acetate can be introduced into a PVA meshwork via an aldehyde group containing a function end-group such as an amine. The amino end-group can be modified into an isocyanate or isothiocyanate. A reactive moieties of a polymer meshwork can be reacted with a function group on the receptor to form a covalent bond. Exemplary functional groups include but are not limited to amine, hydroxy and sulfhydryl.

Similarly, a competitor can be tethered, preferably via a flexible linker, to a polymer meshwork according to any known, suitable methods. Introduction of flexible linkers into a polymer meshwork or a competitor is known to a person skilled in the art. A flexible linker may not have significantly adverse effects on the binding affinity of the competitor to the receptor while eliminating the out-diffusion of the competitor, especially small competitor molecule.

Where the receptor and/or competitor are not covalently bound to the ophthalmic device material which comprises a polymer meshwork containing pores. The pores are of a size which permit the receptor to bind reversibly glucose and/or the receptor, but which prevent the receptor and the competitor from diffusing out of the ophthalmic device. Suitable polymers for this purpose are known in the art and include hydrogels, such as stable polymers of polyethylene glycol hydrogel (PEGH), polyvinylalcohols (PVA), modified polyvinylalcohol (e.g., as nelfilcon A), PVAs with polycarboxylic acids (e.g., carbopol) which may contain crosslinkable functional groups, water-soluble macromer or polymers, starpolymers, dendrimers, and other biopolymers In another embodiment, the ophthalmic device can comprise a glucose-sensing LbL coating which is not covalently attached to the core material of the ophthalmic device, wherein the glucose-sensing LbL coating comprises a testing agent composition which specifically and reversibly interacts with glucose to form a detectable signal which changes in a concentration-dependent manner.

In a preferred embodiment, the glucose-sensing LbL coating comprises at least one layer of a receptor (e.g., a protein or fragment thereof or a chemical compound) that is capable of binding glucose and has a detectable optical signal that changes in a concentration-dependent manner when the receptor is bound to glucose, wherein said detectable optical signal results from one or more labels associated with the receptor. More preferably, the detectable optical signal results from: (1) a fluorescence energy donor and a fluorescence energy acceptor; or (2) a fluorescence energy donor and a non-fluorescence energy acceptor, wherein the energy donor and acceptor are associated with the receptor. As described above, a fluorescent energy donor can be a fluorescent label; a fluorescent energy acceptor can be a fluorescent label; and a non-fluorescent energy donor can be a dye moiety.

In another preferred embodiment, the glucose-sensing LbL coating comprises one or more layers of a receptor having a first label associated therewith and one or more layers of a competitor having a second label associated therewith, wherein one of the first and second labels is a fluorescent energy donor and the other one is a fluorescent or non-fluorescent energy acceptor, wherein each layer of the receptor is separated from each layer of the competitor by one or more spacing polyelectrolyte layers. Each polyelectrolyte layer includes one or more polyelectrolytes, which are generally high molecular weight polymers with multiple ionic or ionizable functional groups.

"LbL coating", as used herein, refers to a coating that is not covalently attached to the surface of an article and is obtained by layer-by-layer ("LbL") deposition of polyelectrolytes on the article. An LbL coating can be a single layer or a bilayer or multiple bilayers.

The term "bilayer" is employed herein in a broad sense and is intended to encompass, a coating structure formed by non-covalently applying first one layer of a first coating material and then one layer of a second coating material having charges opposite the charges of the first coating material. It should be understood that the layers of the first and second coating materials may be intertwined with each other in the bilayer.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

A polycationic material used in the present invention can generally include any material known in the art to have a plurality of positively charged groups along a polymer chain. For instance, suitable examples of such polycationic materials can include, but are not limited to, poly(allylamine hydrochloride) (PAH), poly(ethyleneimine) (PEI), poly(vinylbenzyltriamethylamine) (PVBT), polyaniline (PAN or PANI) (p-type doped) [or sulphonated polyaniline], polypyrrole (PPY) (p-typed doped), and poly(pyridinium acetylene).

A polyanionic material used in the present invention can generally include any material known in the art to have a plurality of negatively charged groups along a polymer chain. For example, suitable polyanionic materials can include, but are not limited to, polymethacrylic acid (PMA), polyacrylic acid (PAA), poly(thiophene-3-acetic acid) (PTAA), poly(4-styrenesulfonic acid) (PSS), sodium poly(styrene sulfonate) (SPS) and poly(sodium styrene sulfonate) (PSSS).

The foregoing lists are intended to be exemplary, but clearly are not exhaustive. A person skilled in the art, given the disclosure and teaching herein, would be able to select a number of other useful polyionic materials.

In order to alter various characteristics of the coating, such as thickness, the molecular weight of the polyionic materials can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

Any suitable LbL polyelectrolyte deposition techniques can be used in the LbL coating. It has been discovered and disclosed in U.S. application Ser. No. 09/005,317 that complex and time-consuming pretreatment of a core material (medical device) is not required prior to non-covalently binding of a polyionic material to the core material. By simply contacting a core material of a medical device, for example, a contact lens, with one or more solutions each containing one or more polyionic materials, an LbL coating can be formed on a medical device to modify the surface properties of the core material of the medical device.

Application of an LbL coating may be accomplished in a number of ways as described in pending U.S. patent applications (application Ser. Nos. 09/005317, 09/774942, 09/775104), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

One dip-coating alternative involves the steps of applying a coating of a first polyionic material to a core material of a medical device by immersing said medical device in a first solution of a first polyionic material; rinsing the medical device by immersing the medical device in a rinsing solution; and, optionally, drying the medical device. This procedure can be repeated using a second polyionic material, with the second polyionic material having charges opposite of the charges of the first polyionic material, in order to form a polyionic bilayer. This bilayer formation process may be repeated a plurality of times in order to produce a thicker LbL coating. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

A sensing layer (receptor or competitor layer) can be prepared by adding a receptor or a competitor into, a coating solution for forming part of a bilayer. When receptor or competitor, which is added into a coating solution, preferably, has a charge. By having a positive or negative charge, the receptor or competitor can be substituted for the charged polymeric material in solution at the same molar ratio. It should be understood, however, that non-charged receptor or competitor can also be applied to the core material of an article by entrapment.

Alternatively, a sensing layer (receptor or competitor layer) can be prepared by first entrapping within a vesicle with a charged surface and then non-covalently applying a layer of the vesicle with a receptor and/or receptor entrapped therein.

In accordance with the present invention, vesicles include liposomes, polymerized micelles, and nanocapsules and microcapsules each having a multilayered shell of polyelectrolytes. The entrapment of a receptor and/or competitor in a vesicle can be carried out according to any known suitable method. Then, an LbL coating can be formed on an article by any suitable known layer-by-layer deposition technique to contain at least one bilayer of a vesicle with a charged surface and with a receptor and a competitor entrapped therein and a polyionic material having charges opposite of the charges of the vesicle.

In another preferred embodiment, the glucose-sensing LbL coating comprises one or more layers of a vesicle with a charged surface and with a receptor and a competitor entrapped therein, wherein the receptor has a first label associated therewith and the competitor has a second label associated therewith, wherein one of the first and second labels is a fluorescent energy donor and the other one is a fluorescent or non-fluorescent energy acceptor. Each polyelectrolyte layer includes one or more polyelectrolytes, which are generally high molecular weight polymers with multiple ionic or ionizable functional groups.

The sensing layers (receptor layers and/or competitor layers) and spacing polyelectrolyte layers are deposited as uniform thin films (1-10 nm) in 10-15 deposition cycles onto the core material of an ophthalmic device, resulting in only a 100-500 nm thick coating for the sensing film, which is highly biocompatible. A typical sequence for construction of an ophthalmic lens suitable for glucose detection involves a deposition cycle of ultrathin (1-10 nm) films of PAA, PAH, PAA, concanavalin A, PAA, PAH, PAA, fluorescein dextran, PAA, PAH, PAA, concanavalin A, PAA, fluorescein dextran, PAA, etc.

The invention, in a still further aspect, provides a kit for screening for diabetes, the kit comprising: (1) a glucose-sensing ophthalmic device, wherein the glucose-sensing ophthalmic device comprises a testing agent composition which specifically and reversibly interacts with glucose to form a detectable signal which changes in a concentration-dependent manner; or (2) two or more tear-collecting devices selected from the group consisting of a strip, a capillary tube, and a soft-hydrogel contact lens, and a testing agent composition which specifically reacts or interacts with glucose to form a detectable signal which changes in a concentration-dependent manner, wherein said strip has a first end and an opposite second end and preferably has substantially uniform cross-sections from the first end to the second end, wherein said strip is made of a hydrogel material in a substantially dry state and is characterized by having a substantially uniform swelling along the hydrogel strip from the first end to the second end when fully wicked by a tear fluid and by having a correlation between the volume of tear uptake by said strip and the length of a tear-wicked end portion of said strip.

Methods of kits of the invention according to embodiments of the invention are useful for rapid screening for diabetes. For example, screenings for diabetes can be carried as follows.

In an in vitro screening assay, subjects could come into an eye practitioner with or without fasting and have a tear sample taken using a first strip of the invention. The subject would then be given an oral carbohydrate load (e.g. 75 g of glucose) and a subsequent sample taken with a second strip of the invention after a defined time period (e.g. from 15 minutes to 30 minutes). The wicked portion of each of the first and second strips would be assayed for glucose, and, if there was a substantial rise in the tear glucose value during that time interval (e.g. 1.5 fold), then the person would be referred for follow-up and diagnosis to a general physician. No follow-up would be required if the person did not get this rise in tear glucose.

In an in vivo screening assay, subjects could come into an eye practitioner with or without fasting and have a tear sample taken using a first strip of the invention. The subject would then be given an oral carbohydrate load (e.g. 75 g of glucose) and a subsequent sample taken with a second strip of the invention after a defined time period (e.g. from 15 minutes to 30 minutes). The wicked portion of each of the first and second strips would be assayed for glucose, and, if there was a substantial rise in the tear glucose value during that time interval (e.g. 1.5 fold), then the person would be referred for follow-up and diagnosis to a general physician. No follow-up would be required if the person did not get this rise in tear glucose.

The previous disclosure will enable one having ordinary skill in the art to practice the invention. In order to better enable the reader to understand specific embodiments and the advantages thereof, reference to the following examples is suggested.

EXAMPLE 1

A tear sample is collected using a microcapillary tube from a fasting subject before being given orally a 54 g carbohydrate load. Another tear sample is collected from the same subject at every 15 minutes after oral administration of the carbohydrate load. The last tear sample is collected at 180 minutes after oral administration of the carbohydrate load. 12 subjects (3 normals, 9 diabetics) have been screened. Glucose concentration, in these tear samples, is measured using a modified Amplex Red Assay (glucose oxidase and peroxidase, with a fluorescent substrate). FIG. 1 shows the average tear glucose values (+Standard Deviations) between normals and diabetics every 15 minutes. At 15 minutes, there is noticeable difference between normals and diabetics. At 30, 45 and 60 minutes there is definitively a statistically significant difference between normals and diabetics.

What is claimed is:

1. A kit for rapid screening of diabetes, the kit comprising: a glucose-sensing ophthalmic device and instructions for using the glucose-sensing ophthalmic device to screen for diabetes, wherein the glucose-sensing ophthalmic device comprises a testing agent composition which specifically and reversibly interacts with glucose to form a detectable optical signal which changes in a concentration-dependent manner, wherein the testing agent composition comprises a receptor having a first label associated therewith and a competitor having a second label associated therewith, wherein one of the first and second labels is a fluorescent energy donor and the other one is a fluorescent or non-fluorescent energy acceptor, wherein the ophthalmic device comprises a glucose-sensing layer-by-layer coating which is not covalently attached to the core material of the ophthalmic device, and wherein the glucose-sensing layer-by-layer coating comprises one or more layers of a vesicle with a charged surface and with the receptor and the competitor entrapped therein.

2. A kit of claim 1, wherein the glucose-sensing layer-by-layer coating comprises one or more layers of a vesicle with a charged surface and with a receptor entrapped therein, wherein the receptor is capable of reversibly binding glucose and has a detectable optical signal that changes in a concentration-dependent manner when the receptor is reversibly bound to glucose, wherein said detectable optical signal results from one or more labels associated with the receptor.

3. A kit of claim 2, wherein the detectable optical signal results from a pair of labels associated with the receptor, a first label and a second label, wherein one of the first and second label is a fluorescence energy donor and the other is a fluorescence energy acceptor or a non-fluorescence energy acceptor.

* * * * *